United States Patent
Heise et al.

(10) Patent No.: US 8,941,916 B2
(45) Date of Patent: Jan. 27, 2015

(54) FILTER HOLDER FOR CORRELATIVE PARTICLE ANALYSIS

(71) Applicant: Carl Zeiss Microscopy GmbH, Jena (DE)

(72) Inventors: Heino Heise, Adelebsen (DE); Ulrich Kohlhaas, Goettingen (DE)

(73) Assignee: Carl Zeiss Microscopy GmbH, Jena (DE)

( * ) Notice: Subject to any disclaimer, the term of this patent is extended or adjusted under 35 U.S.C. 154(b) by 271 days.

(21) Appl. No.: 13/656,277

(22) Filed: Oct. 19, 2012

(65) Prior Publication Data

US 2013/0100526 A1    Apr. 25, 2013

(30) Foreign Application Priority Data

Oct. 21, 2011   (DE) .......................... 10 2011 117 134

(51) Int. Cl.
*G02B 21/26* (2006.01)
*G02B 21/34* (2006.01)
*G01N 1/28* (2006.01)
*G01N 15/06* (2006.01)
*G01N 15/00* (2006.01)

(52) U.S. Cl.
CPC .............. *G02B 21/34* (2013.01); *G01N 1/2813* (2013.01); *G01N 15/0625* (2013.01); *G01N 2015/0042* (2013.01)
USPC ......................................... 359/391; 359/892

(58) Field of Classification Search
CPC . G02B 21/34; G01N 1/2813; G01N 15/0625; G01N 2015/0042
USPC .................................. 359/368, 381, 391, 892
See application file for complete search history.

(56) References Cited

U.S. PATENT DOCUMENTS

| | | | |
|---|---|---|---|
| 4,003,135 A | 1/1977 | Baker et al. | |
| 4,744,667 A * | 5/1988 | Fay et al. | 356/417 |
| 4,972,258 A * | 11/1990 | Wolf et al. | 348/79 |
| 5,409,832 A | 4/1995 | Pocock | |
| 6,563,113 B1 * | 5/2003 | Amann et al. | 250/309 |
| 6,750,039 B1 | 6/2004 | Bargoot | |
| 2011/0250633 A1 * | 10/2011 | Jansen | 435/39 |

FOREIGN PATENT DOCUMENTS

| | | |
|---|---|---|
| DE | 31 03 865 A1 | 9/1982 |
| EP | 0800199 A2 | 10/1997 |
| JP | 2011-197040 A | 10/2011 |

OTHER PUBLICATIONS

EP Search Report Dated Jan. 24, 2013, Related to EP Application No. 12187884.7.2217, 5 Pgs.

* cited by examiner

*Primary Examiner* — Frank Font
(74) *Attorney, Agent, or Firm* — Patterson Thuente Pedersen, P.A.

(57) ABSTRACT

A filter holder for correlative particle analysis during imaging microscopy methods or methods of the elemental analysis including a receiving element with a filter support and a fastening unit. The plane filter support is designed as pressure piece and is movably arranged in the receiving element to be movable at a right angle to the surface of the filter for the purpose of tensioning the filter. The fastening unit includes a clamping element which encloses the filter at the circumference of the filter and is held by a tensioning element which is supported in the receiving element.

15 Claims, 4 Drawing Sheets

FILTER HOLDER FOR CORRELATIVE PARTICLE ANALYSIS

CLAIM TO PRIORITY

This application claims the benefit of German Patent Application DE 102011117134.0 filed Oct. 21, 2011 the entire contents of which are incorporate by reference herein.

FIELD OF THE INVENTION

The invention relates to a filter holder for correlative particle analysis during imaging microscopy methods or methods of elemental analysis, comprising a receiving element with a filter support and a fastening unit.

BACKGROUND

Filter holders with a glass panel are known. In this prior art, a glass panel ground to optical quality and usually coated with an antireflection layer presses the filter made of paper or plastic fabric level or flat onto the filter holder. This is caused either by the weight of the glass panel and the frame, by screw connection, or spring force. This solution is disadvantageous because over time, particularly during the cleaning process, the particles scratch the glass panel which then has to be replaced at great cost. It is further disadvantageous because particles from the filter remain on the glass panel when said panel is removed and a reexamination of the filters yields different results than the results obtained from the first observation. Furthermore, insufficient cleaning poses the risk of adhering particles contaminating the filter to be examined next and thus falsifying the measurement result. However, it is most disadvantageous that filters covered with a glass panel cannot be imaged with an electron microscope and also do not allow for an elemental analysis with X-ray spectroscopy.

Furthermore, filter holders with a clamping ring are known. In this prior art, the filter is retained at the periphery with a tension ring. This is effected either by the weight of the ring, by screw connection, or spring force. This is disadvantageous because the filter material becomes uneven due to the drying process after filtering. The standard microscopic examination is commonly carried out with objectives 5× and 10×. Their low depth of field frequently requires refocusing, particularly in automated analysis systems with a motorized scanning table and a motorized autofocus. In unfavorable cases, the time for the analysis is at least doubled. One advantage of this arrangement over the filter holder with a glass panel is that the filters can be imaged with an electron microscope and an elemental analysis using X-ray spectroscopy is also possible.

SUMMARY OF THE INVENTION

Proceeding from the described disadvantages of the solutions of the prior art, the problem addressed by the invention is that of further developing a filter holder for correlative particle analysis such that, with the advantages of the solutions of the prior art, a cost-effective, quick and reproducible particle analysis on a filter fastened in the orientation of one plane can be performed and verified.

According to the invention, this problem is solved with a filter holder of the type initially described with the features described herein.

According to the invention, the plane filter support which is designed as pressure piece is movably arranged in the receiving element at a right angle to the surface of the filter for the purpose of tensioning the filter, wherein the fastening unit is a clamping element which encloses the filter at the circumference and which is held by a tensioning element supported in the receiving element.

Since circular, disk-shaped filters are commonly used, the clamping element and the tensioning element are designed accordingly in the form of a ring, wherein the tensioning element for generating the tension force of the tensioning element is, in an example embodiment, enclosed by a tension spring which is supported in the receiving element and the spring force of said tension spring acts on the tensioning element.

Screw connections or bayonet locks can also be used as tensioning elements.

Because of the arrangement of the filter, the filter is stretched evenly. No additional covering with a glass panel is required.

The clamping element, according to the invention, does not require tools for fastening the filter, but it also an option according to the invention to screw a fastening plate to the receiving element using a tool.

Due to the planar stretching of the filter, the entire filter surface can be observed without frequent refocusing. This saves significant time when compared to solutions without a plane filter position.

The filter holder can be used without limitations for examinations with a light microscope as well as examinations with an electron microscope, wherein the filter can remain in the filter holder while the stage is changed.

A coordinate system which is marked on the filter holder, and which can also be transported when devices are changed, allows for a precise relocalization of individual particles.

In an example embodiment, the clamping element is provided with an integrated groove structure for the purpose of an uncomplicated seating of the filter, wherein it is also contemplated within the invention to insert slip-resistant structures in the clamping element and the counterpiece.

According to another example embodiment, the connecting surfaces between the clamping element and the tensioning element have interlocking wave structures to ensure a firm fastening of the filter in the filter holder.

This type of fastening of the filter thus ensures a secure clamping and tensioning in the plane without causing damage to the filter.

According to another example embodiment, at least two bores offset by other than 180 degrees, which allow for a punching of corresponding holes in the filter and which are used for receiving reference pins, are present for the purpose of positioning the filter between the tensioning element and the clamping element.

During verification of the examination results, the reference pins, which then engage in the punched holes in the filter, allow for the filter to be inserted in the filter holder in the same position in order to redetect the particles marked in the aforementioned coordinate system.

It is also within the invention to orientate the filter using known positioning means such as stops, etc.

In another example embodiment for tensioning the filter, the plane filter support which is designed as pressure piece can be positioned vertically without a rotary movement, wherein a worm gear with bevel gearing can be used which is attached to the pressure piece via a thread, and a pinion disposed in the receiving element engages in the bevel gearing.

The worm gear is designed such that a sensitive vertical movement and thus a sensitive filter tension are possible.

It is also within the invention that the movement of the pressure piece is realized with other known movement mechanisms. For example, a wedge-shaped piece movable in a horizontal direction can be used in another example embodiment.

For the constant use of similar filters, the plane filter support expediently designed as pressure piece can press against the filter with constant spring force using a spring element.

BRIEF DESCRIPTION OF THE DRAWINGS

In the following, the filter holder according to the invention is further explained.

DETAILED DESCRIPTION

Figure 1:
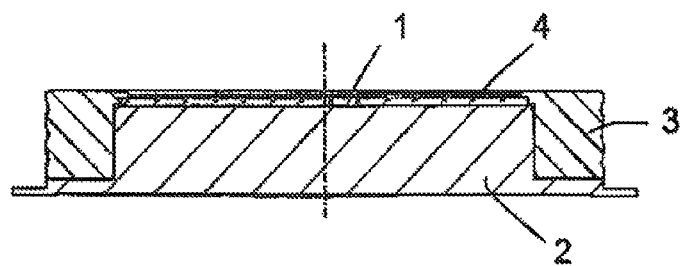
FIG. 1 is a schematic depiction of a filter holder with a glass panel according to the prior art.

FIG. 1 shows a solution of the prior art with a filter 1, which is arranged on a plane filter support 2 and fastened to a glass panel 4 by the weight of a frame 3, wherein the fastening is also possible with the use of screw connections or spring elements. As already described in the prior art, this solution is disadvantageous because due to frequent filter changes, particularly during the cleaning process, the particles scratch the glass panel which then has to be replaced at great cost.

However, it is most disadvantageous that filters covered with a glass panel cannot be imaged with an electron microscope and also do not allow for an elemental analysis with X-ray spectroscopy.

Figure 2:
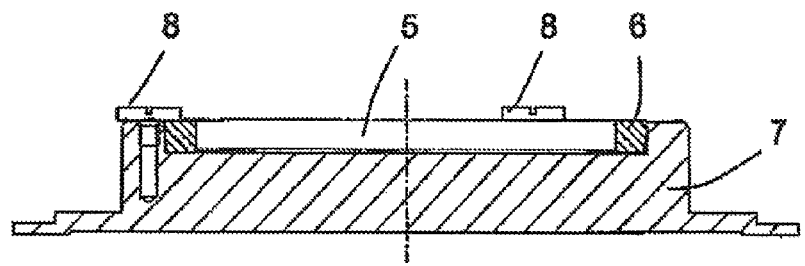
FIG. 2 is a schematic depiction of a filter holder with a clamping ring according to the prior art.

FIG. 2 describes a further solution according to the prior art which shows a filter 5 positioned at the periphery with a clamping ring 6 on a filter support 7. The clamping ring 6 is commonly fastened vertically using screw connections 8.

As initially described, this solution is disadvantageous because the filter material becomes uneven due to the drying process after filtering. Furthermore, frequent refocusing is required particularly in automated analysis systems with a motorized scanning table and a motorized autofocus.

Figure 3:
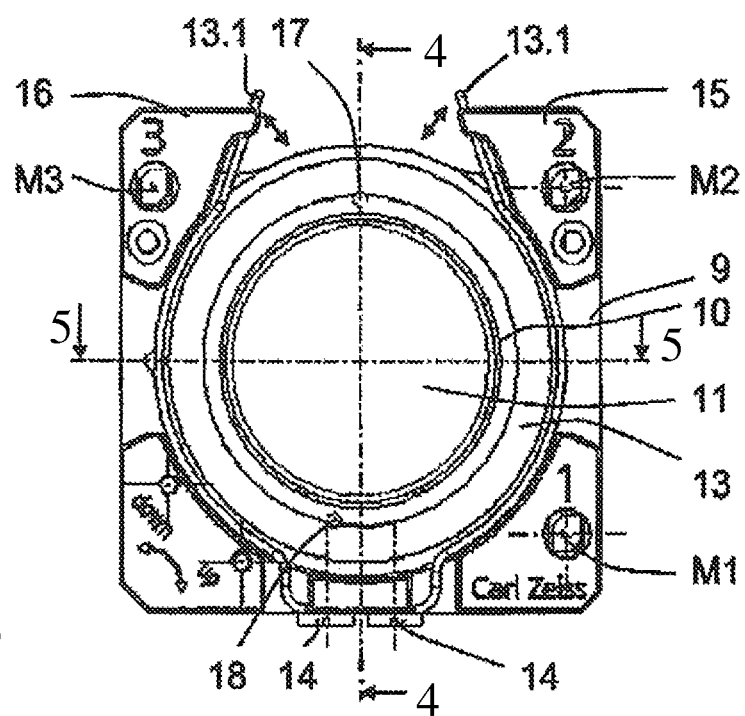
FIG. 3 is a schematic depiction of a filter holder according to an example embodiment of the invention as viewed from the top.

FIG. 3 shows a filter holder, according to the invention, as viewed from the top with a receiving element 9, in which a circular, disk-shaped filter 10 is placed on a filter support 11 which is designed as pressure piece.

The filter 10 is held in the receiving element 9 by a clamping element 12 which encloses the filter at the circumference and fastened using a tensioning element 13 with a tension spring 13.1, which acts on the tensioning element 13.

The tension spring 13.1 is connected to the receiving element 9 using fastening screws 14.

Furthermore, FIG. 3 shows two reference pins 17 and 18 offset by other than 180 degrees, which are arranged in the receiving element 9 and engage in corresponding openings in the filter 10 for the purpose of its positioning (rotation prevention). The surface of the receiving element 9 has three markings M1, M2, M3 for a marked coordinate system which can also be transported when devices are changed in order to allow for a precise relocalization of individual particles.

Figure 4:
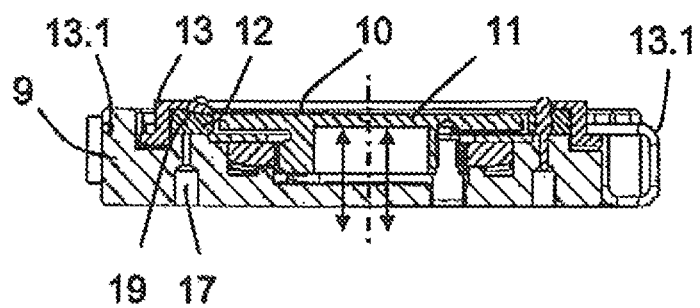
FIG. 4 depicts a cross-sectional view taken along section line 4-4 of the filter holder of FIG. 3.

FIG. 4 shows a cross-sectional view 4-4 of the filter holder in FIG. 3 with the detailed view of the filter support 11, which is designed as pressure piece, the arrangement of the filter 10, the clamping element 12, the tension spring 13.1, and the tensioning element 13.

The connecting surfaces between the clamping element 12 and the tensioning element 13 have interlocking wave structures 19.

Figure 5:
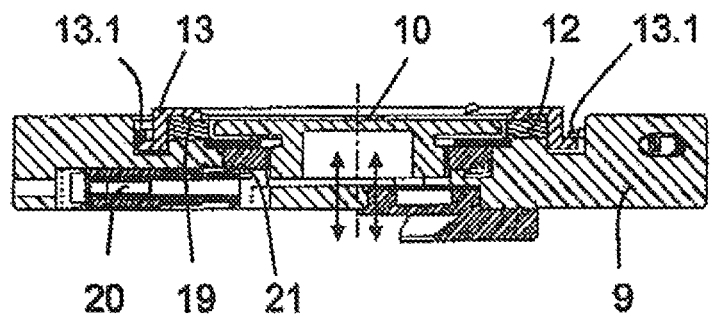
FIG. 5 depicts a cross-sectional view taken along 5-5 of the filter holder of FIG. 3.

FIG. 5 shows a cross-sectional view 5-5 from FIG. 3, depicting not only the single elements shown in FIG. 4 but also an adjusting screw 20 for the vertical movement change without a rotary movement of the filter support 11 which is designed as pressure piece. Therefore, by actuating the adjusting screw 20, the filter 10 is tensioned or slackened via a schematically depicted worm gear 21.

Figure 6:
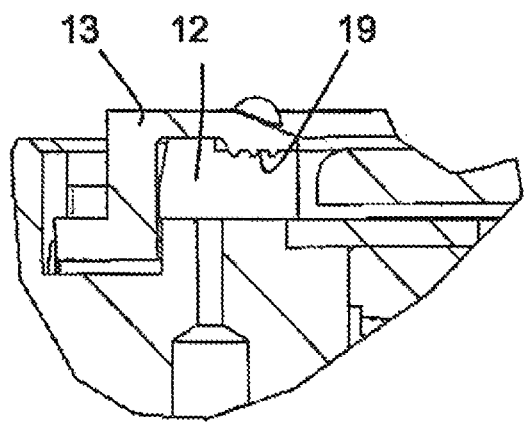
FIG. 6 is a schematic depiction of the fastening unit.

FIG. 6 shows a magnified depiction of the fastening unit with the tensioning element 13, the clamping element 12 and the wave structures 19 of the connecting surfaces, wherein the filter 10 is held by the wave structures 19 (not shown in FIG. 5). The filter 10 is oriented such that the filter is first placed in the filter holder. Then the holes for receiving the reference pins 17 and 18 are punched. Now the filter 10 is once again removed. After introducing the reference pins 17 and 18, the filter 10 is again placed in the filter holder and positioned in the same position as the initial placement using the holes and reference pins 17 and 18.

Figure 7:
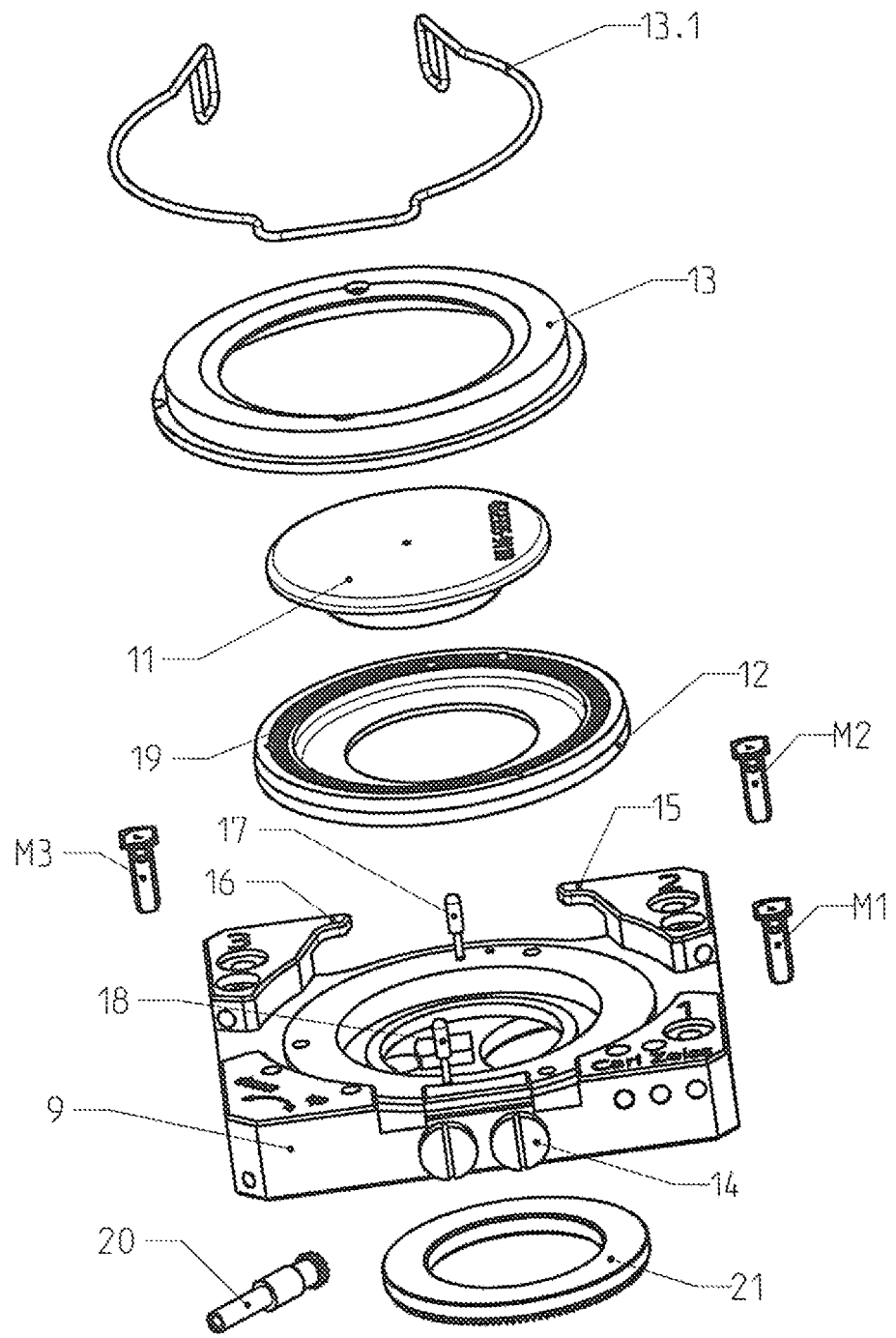
FIG. 7 is an exploded perspective view of the filter holder according to an example embodiment of the invention.

FIG. 7 is an exploded perspective view of a filter holder according to an example embodiment of the invention including receiving element 9, filter support 11, clamping element 12 and tensioning element 13. Tensioning element 13 also includes tension spring 13.1 which is coupled to fastening screws 14. Limbs 15 and 16 of receiving element 9 are structure to receive tension spring 13.1 when tension spring 13.1 is compressed for insertion since tension spring 13.1 is biased toward an outward direction. Reference pins 17 and 18 are removably received into receiving element 9. Wave structure 19, adjusting screw 20, worm gear 21 and marking M1, M2 and M3 are as previously described.

The present invention may be embodied in other specific forms without departing from the spirit of the essential attributes thereof; therefore, the illustrated embodiments should be considered in all respects as illustrative and not restrictive, reference being made to the appended claims rather than to the foregoing description to indicate the scope of the invention.

LIST OF REFERENCE SIGNS 1, 5, 10 Filter
2, 7, 11 Filter support
3 Frame
4 Glass panel
6 Clamping ring
8 Screw connection
9 Receiving element
12 Clamping element
13 Tensioning element
13.1 Tension spring
14 Fastening screws
15, 16 Limb
17, 18 Reference pins
19 Wave structure
20 Adjusting screw
21 Worm gear
M1, M2, M3 Markings The inventin claimed is:

1. A filter holder for correlative particle analysis during imaging microscopy methods or methods of elemental analysis, comprising:
   a receiving element with a filter support and a fastening unit;
   wherein the filter support includes a plane filter support designed as pressure piece that is movably arranged in the receiving element to be movable at a right angle to the surface of a filter thereby tensioning the filter; and
   wherein the fastening unit comprises a clamping element which engages the filter proximate a circumference of the filter and wherein the filter is held by a tensioning element which is supported in the receiving element.

2. The filter holder for correlative particle analysis according to claim 1, wherein the clamping element and the tensioning element are designed in the form of a ring when circular, disk-shaped filters are used.

3. The filter holder for correlative particle analysis according to claim 1, wherein the tensioning element includes a tension spring that generates a tension force of the tensioning element and is supported in the receiving element and further wherein a spring force of the tension spring acts on the tensioning element.

4. The filter holder for correlative particle analysis according to claim 2, wherein the tensioning element includes a tension spring that generates a tension force of the tensioning element and is supported in the receiving element and further wherein a spring force of the tension spring acts on the tensioning element.

5. The Filter holder for correlative particle analysis according to claim 1, wherein the clamping element presents an integrated groove structure for the purpose of seating the filter.

6. The Filter holder for correlative particle analysis according to claim 2, wherein the clamping element presents an integrated groove structure for the purpose of seating the filter.

7. The filter holder for correlative particle analysis according to claim 1, wherein the connecting surfaces between the clamping element and the tensioning element have interlocking wave structures.

8. The filter holder for correlative particle analysis according to claim 2, wherein the connecting surfaces between the clamping element and the tensioning element have interlocking wave structures.

9. The filter holder for correlative particle analysis according to claim 3, wherein the connecting surfaces between the clamping element and the tensioning element have interlocking wave structures.

10. The filter holder for correlative particle analysis according to claim 4, wherein the connecting surfaces between the clamping element and the tensioning element have interlocking wave structures.

11. The filter holder for correlative particle analysis according to claim 1, further having at least two bores offset by other than 180 degrees that position the filter between the tensioning element and the clamping element and wherein the bores allow for a punching of corresponding holes in the filter which are used for receiving reference pins received in the bores.

12. Filter holder for correlative particle analysis according to claim 1, wherein the plane filter support which is designed as pressure piece can be positioned vertically without a rotary movement.

13. The filter holder for correlative particle analysis according to claim 12, further comprising a worm gear used for the vertical movement of the pressure piece which comprises a bevel gearing which is attached to the filter support via a thread and a pinion with an adjusting screw which is disposed in the receiving element and engages in the bevel gearing.

14. The filter holder for correlative particle analysis according to claim 12, wherein vertical movement of the filter support, which is designed as a pressure piece is realized using a wedge-shaped piece which is movable in a horizontal direction.

15. The filter holder for correlative particle analysis according to claim 1, wherein the plane filter support which is designed as pressure piece presses with constant spring force against the filter using a spring element.

* * * * *

UNITED STATES PATENT AND TRADEMARK OFFICE
CERTIFICATE OF CORRECTION

PATENT NO. : 8,941,916 B2  
APPLICATION NO. : 13/656277  
DATED : January 27, 2015  
INVENTOR(S) : Heino Heise et al.

Page 1 of 1

It is certified that error appears in the above-identified patent and that said Letters Patent is hereby corrected as shown below:

In the claims,

Col. 6, line 21, delete "Filter" and insert --The filter--

Signed and Sealed this  
First Day of March, 2016

Michelle K. Lee  
*Director of the United States Patent and Trademark Office*